(12) United States Patent
Howe

(10) Patent No.: US 7,209,837 B2
(45) Date of Patent: Apr. 24, 2007

(54) SYSTEMS AND METHODS FOR DETERMINING COMPENSATED CONDUCTIVITIES

(75) Inventor: Spencer Howe, Scituate, MA (US)

(73) Assignee: Invensys Systems, Inc., Foxboro, MA (US)

(*) Notice: Subject to any disclaimer, the term of this patent is extended or adjusted under 35 U.S.C. 154(b) by 223 days.

(21) Appl. No.: 10/860,917

(22) Filed: Jun. 4, 2004

(65) Prior Publication Data
US 2005/0273293 A1 Dec. 8, 2005

(51) Int. Cl.
*G01N 31/00* (2006.01)

(52) U.S. Cl. .................. 702/23; 702/85; 73/61.41

(58) Field of Classification Search ............ 702/23–26, 702/30–32, 50, 53, 85–88, 99, 130, 133–136; 73/1.01–1.03, 53.01, 61.41–61.93
See application file for complete search history.

(56) References Cited

U.S. PATENT DOCUMENTS

| 5,618,644 A | * | 4/1997 | Morita ...................... 430/30 |
| 6,643,610 B1 | | 11/2003 | Kleven et al. ............. 702/183 |
| 2001/0031501 A1 | * | 10/2001 | Nomura et al. ............ 436/149 |
| 2003/0037590 A1 | * | 2/2003 | Stark ......................... 73/1.03 |
| 2004/0265174 A1 | * | 12/2004 | Mehus et al. ............... 422/67 |

* cited by examiner

*Primary Examiner*—Manuel L. Barbee
(74) *Attorney, Agent, or Firm*—Foley Hoag LLP

(57) ABSTRACT

The disclosed systems and methods determine compensation factors, compensated conductivities, concentrations, and other related parameters of a solution based on the solution's temperature and absolute conductivity.

27 Claims, 6 Drawing Sheets

SYSTEMS AND METHODS FOR DETERMINING COMPENSATED CONDUCTIVITIES

BACKGROUND

Solutions in which a chemical is dissolved in water are commonly referred to as aqueous solutions. Some aqueous solutions conduct electricity; this property is referred to as conductivity. The conductivity of an aqueous solution depends on the solution's concentration, which is a ratio between the amounts of chemical and water in the solution, and the solution's temperature.

The conductivities of some concentrations of some species (i.e., chemical types) of aqueous solutions are well known. For example, the conductivities of many different concentrations of sulfuric acid have been measured at several temperatures by Darling and other researchers. These conductivities are often presented in the form of reference conductivity curves. A reference conductivity curve shows the relationship between conductivity and concentration for a species of aqueous solution at a reference temperature. FIG. 6 shows reference conductivity curves for sulfuric acid at reference temperatures of 0° C., 18° C., or 25° C.

Since the conductivity of an aqueous solution depends on its concentration, a measurement of conductivity is often used to deduce concentration. This measurement is compensated for temperature by scaling it to the conductivity that the solution would have if the temperature of the solution were brought to the reference temperature of a reference conductivity curve for the species (e.g., 0° C., 18° C., or 25° C. for the curves for sulfuric acid shown in FIG. 6). This scaling depends solely on temperature and results in a compensated conductivity. The compensated conductivity is then compared to the reference conductivity curve, and the concentration of the solution is determined to be the reference concentration whose reference conductivity most closely approaches the compensated conductivity.

The ratio between absolute conductivity and compensated conductivity is usually referred to as the temperature compensation factor. The temperature compensation factor for most species of aqueous solutions depends relatively strongly on temperature and relatively weakly on concentration. As such, computing the temperature compensation factor based solely on temperature, but not on concentration, is sufficient for ordinary applications, e.g., applications that do not require high degrees of accuracy. (In other words, assuming that different concentrations of a solution have the same temperature compensation factor is usually a sufficient approximation for ordinary applications.) Computing the temperature compensation factor based solely on temperature is not sufficient, though, for applications that require high degrees of accuracy.

Unfortunately, while a solution's temperature can be measured prior to compensating the solution's conductivity, the solution's concentration cannot be determined until after compensation. Present scenarios for determining compensated conductivities, compensation factors, concentrations, and other related solution parameters have, therefore, limited accuracy.

SUMMARY

Generally, the disclosed systems and methods can determine a temperature compensation factor for a solution based on the solution's temperature and absolute conductivity, rather than just the solution's temperature. The disclosed systems and methods facilitate increased accuracy determinations of compensation factors, compensated conductivities, concentrations, and other related solution parameters. The disclosed systems and methods can be applied to aqueous solutions (e.g., solutions in which one or more chemicals are dissolved in water) and non-aqueous solutions (e.g., solutions in which one or more chemicals are dissolved in a solvent that includes a non-water component).

Methods for determining concentrations and other related solution parameters are described. In embodiments, reference conductivities of reference concentrations of a solution at a reference temperature are provided. Based on the solution's temperature and conductivity, a conversion factor for converting the conductivity to a compensated conductivity at the reference temperature is determined. Based on the conversion factor and the conductivity, the compensated conductivity of the solution is computed. The concentration is then determined based on the compensated conductivity, the reference conductivities, and the reference concentrations.

In one embodiment, pre-determined conversion factors that are associated with conductivities and temperatures are provided and the conversion factor is determined based on the pre-determined conversion factor that is associated with the solution's conductivity and temperature. Alternatively, the conversion factor is determined based on interpolating between pre-determined conversion factors. The pre-determined conversion factors may be provided in a look-up table.

In one embodiment, an expression for the conversion factor is provided and the conversion factor is determined based on computing a value of the expression for the solution's conductivity and temperature.

In some embodiments, the expression is generated based on the following scenario. The conductivities of a group of different concentrations of the solution are provided at the reference temperature and non-reference temperatures. For each non-reference temperature and each different concentration in the group, a ratio is determined between the conductivity of the concentration at the non-reference temperature and the conductivity of the concentration at the reference temperature (or vice-versa). A relationship is then determined among the ratios, the conductivities of the different concentrations, and the temperature.

In an embodiment, the compensated conductivity is computed based on a product of the conductivity and the conversion factor or its reciprocal.

In embodiments, the methods further include calibrating the conductivity prior to determining the conversion factor. In one aspect, a conversion factor for converting a reference conductivity of the solution at a reference temperature to an estimated conductivity of the solution at a solution temperature is determined. An estimated conductivity at the solution temperature is computed based on the reference conductivity and the conversion factor. The conductivity is then calibrated based on a measure of the difference between the conductivity and the estimated conductivity.

Devices for determining chemical concentrations and other related solution parameters are also described. In embodiments, the devices include digital data processing devices that are in communication with the reference data for the solution and that are configured to execute features of the previously described methods.

Processor-readable mediums including instructions for determining chemical concentrations and other related solution parameters are also described. The processor-readable mediums include instructions to cause a processor to execute features of the previously described methods.

Systems for determining chemical concentrations and other related solution parameters are also described. In embodiments, the systems include a temperature sensor, a conductivity sensor, a digital data processing device in communication with the temperature and conductivity sensors, and a medium that can be read by the digital data processing device and that includes reference data and instructions for causing the digital data processing device to execute features of the previously described methods. In some embodiments, the systems further include a display and/or an alarm in communication with the digital data processing device.

These and other features of the disclosed systems and methods can be more fully understood by referring to the following detailed description and accompanying drawings.

DESCRIPTION

Figure 1:
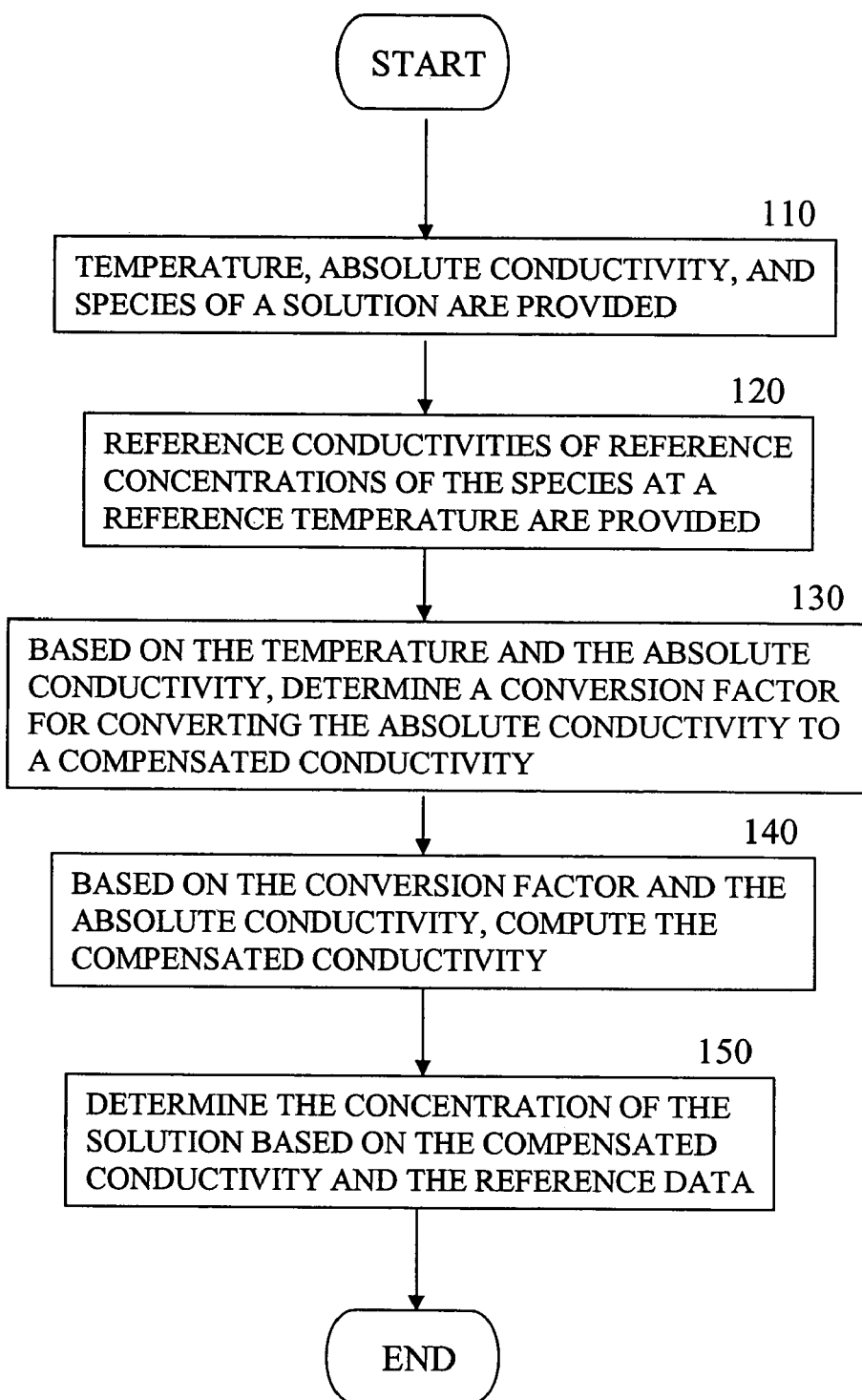
FIG. 1 is a flow chart that illustrates an exemplary method for determining a concentration of a solution.

Illustrative embodiments will now be described to provide an overall understanding of the disclosed systems and methods. One or more examples of the illustrative embodiments are shown in the drawings. Those of ordinary skill in the art will understand that the disclosed systems and methods can be adapted and modified to provide systems and methods for other applications, and that other additions and modifications can be made to the disclosed systems and methods without departing from the scope of the present disclosure. For example, features of the illustrative embodiments can be combined, separated, interchanged, and/or rearranged to generate other embodiments. Such modifications and variations are intended to be included within the scope of the present disclosure.

FIG. 1 is a flow chart that illustrates an exemplary method for computing a concentration of a solution. As will be understood by those of ordinary skill in the art, the disclosed systems and methods are not limited to the flow elements shown in FIG. 1 and can compute a concentration of a solution based on one or more flow elements that are different than and/or additional to those shown in FIG. 1.

As shown in FIG. 1, the temperature, conductivity, and species of a solution are determined, measured, or otherwise provided based on schemes known to those of ordinary skill in the art (110 in FIG. 1). This conductivity is usually referred to as the absolute conductivity of the solution. For example, the temperature and absolute conductivity can be measured using well known sensors. In most embodiments, the species is known a priori. In some embodiments, however, the species may be determined using filter paper or other well known techniques. Reference conductivities and reference concentrations of the species at a reference temperature are also provided (120 in FIG. 1). Such reference data may be provided in the form of a reference conductivity curve for the species, similar to one of the curves shown in FIG. 6. Alternatively or in combination, such reference data may be provided in another form, such as in one or more data structures, e.g., look-up tables.

As also shown in FIG. 1, a temperature compensation factor for converting the absolute conductivity of the solution at the solution's temperature to a compensated conductivity of the solution at the reference temperature is then determined based on the solution's temperature and absolute conductivity (130 in FIG. 1). For reference, the temperature compensation factor is referred to herein as a conversion factor.

In most embodiments, the conversion factor is determined by computing a value of an expression that was previously deduced from empirical data for the species of the solution and that represents the factor as a function of solution temperature and absolute conductivity. Schemes for generating the expression are described further herein with respect to FIGS. 2–4.

Alternatively, in some embodiments, the conversion factor is determined by referring to one or more data structures (e.g., look-up tables) that include pre-determined conversion factors that are indexed to and/or otherwise associated with solution temperatures and absolute conductivities. In some embodiments, the pre-determined conversion factors may simply be empirical measurements of those factors, e.g., measurements of the ratios and other data in FIG. 2 (220). Alternatively and/or in combination, in some embodiments, the pre-determined conversion factors may be computed values of the above expression. In at least some of the foregoing types of embodiments, determining the conversion factor includes determining whether one of the pre-determined conversion factors is associated with the solution's temperature and absolute conductivity. If one of the pre-determined conversion factors is so associated, then the conversion factor for the solution is determined to be the one of the pre-determined conversion factors. If none of the pre-determined conversion factors is so associated, however, then the conversion factor is determined based on interpolating between pre-determined conversion factors.

As further shown in FIG. 1, the compensated conductivity is then computed based on the absolute conductivity and the conversion factor (140 in FIG. 1). In most embodiments, the conversion factor is a ratio between absolute conductivity and compensated conductivity, and the compensated conductivity is computed based on the product of the absolute conductivity and the reciprocal of the conversion factor. In some embodiments, the conversion factor is a ratio between compensated conductivity and absolute conductivity, and the compensated conductivity is computed based on the product of the absolute conductivity and the conversion factor.

With continuing reference to FIG. 1, the concentration of the solution is ultimately determined based on the compensated conductivity, the reference data, and schemes known to those of ordinary skill in the art (150 in FIG. 1). For example, in some embodiments, the concentration of the solution is determined to be that reference concentration whose reference conductivity is equal to, most nearly equal to, or otherwise closely approaches the compensated conductivity.

Figure 2:
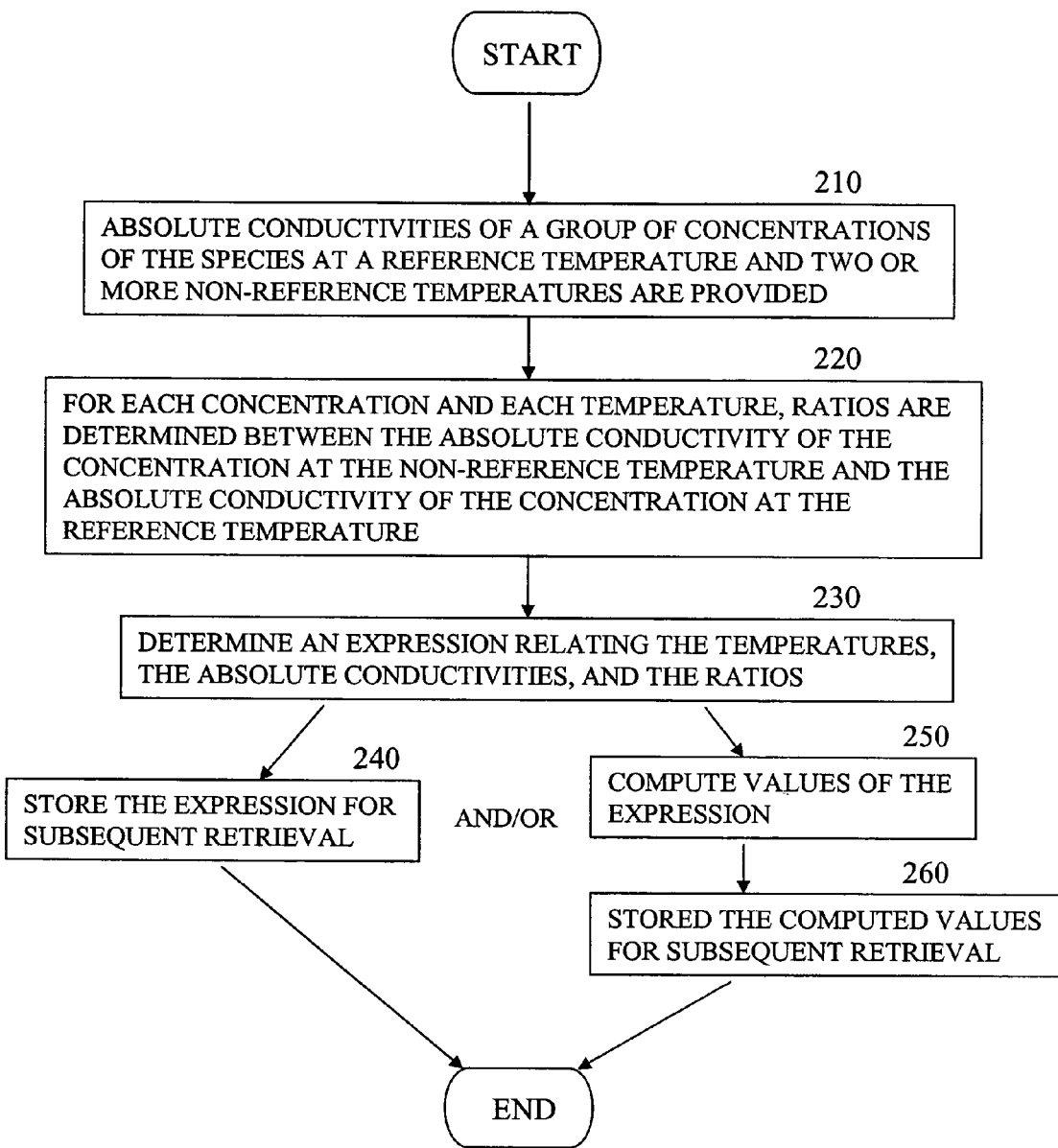
FIG. 2 is a flow chart that illustrates an exemplary method for determining a temperature compensation factor of a solution.

FIG. 2 is a flow chart that illustrates an exemplary method for generating an expression for the conversion factor, i.e., the factor for converting the solution's absolute conductivity at the solution's temperature to a compensated conductivity of the solution at the reference temperature. As previously described, in most embodiments, the flow elements of FIG. 2 are performed prior to the flow elements of FIG. 1, so that the expression and/or computed values of the expression may be used on "live" data in FIG. 1 (130). As will be understood by those of ordinary skill in the art, the disclosed systems and methods are not limited to the flow elements shown in FIG. 2 and can compute a conversion factor based on one or more flow elements that are different than and/or additional to those shown in FIG. 1.

Figure 6:
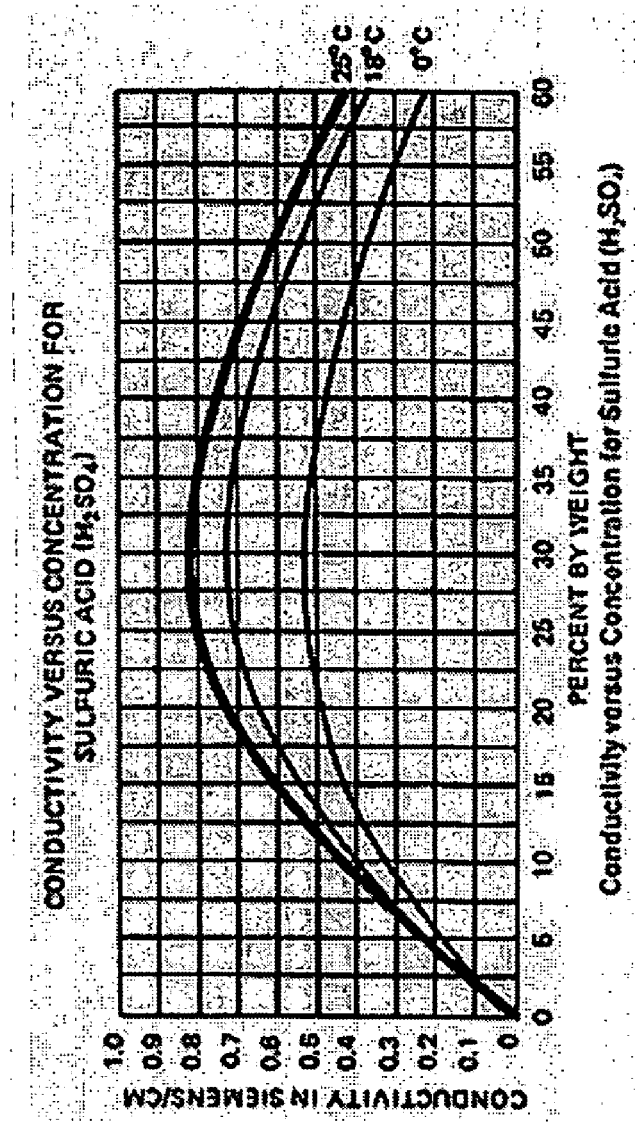

As shown in FIG. 2, empirical data for the species of the solution are determined, measured, or otherwise provided (210 in FIG. 2). The empirical data include absolute conductivities of a group of concentrations of the species at (i) a temperature that will be selected as the reference temperature and (ii) at least two other temperatures (and, in most embodiments, between ten and twenty temperatures) referred to as non-reference temperatures. For some species, the empirical data is available in one or more published reference sources known to those of ordinary skill in the art. (For example, the data for sulfuric acid shown in FIG. 6 is based on published data by Darling and other researchers.) For other species, the empirical data may be acquired by direct measurement. The group of concentrations includes several different concentrations over a range of concentrations to allow the behavior of absolute conductivity with concentration at the reference temperature and each of the non-reference temperatures to be deduced with a degree of certainty that is reasonable to one of ordinary skill in the art. While data at relatively few concentrations (e.g., five) may be enough to deduce the behavior for some species at a given temperature, data at relatively more concentrations (e.g., fifteen) may be necessary to deduce the behavior of other species at the given temperature.

As also shown in FIG. 2, based on the empirical data, ratios are determined between the conductivities at the non-reference temperatures and the conductivities at the reference temperature (220 in FIG. 2). Generally, for each temperature in the empirical data (i.e., the reference temperature and each of the non-reference temperatures) and each concentration in the empirical data, a ratio is determined between the absolute conductivity of that concentration at that temperature and the absolute conductivity of that concentration at the reference temperature. In some embodiments, the reciprocal of this ratio is determined. Accordingly, a result is a set of ordered triplets for each concentration in the empirical data, namely, temperature, the concentration's absolute conductivity at that temperature, and a ratio between the concentration's absolute conductivity at that temperature and its absolute conductivity at the reference temperature. It can be recognized that this ratio is unity for the reference temperature itself.

Figure 3:
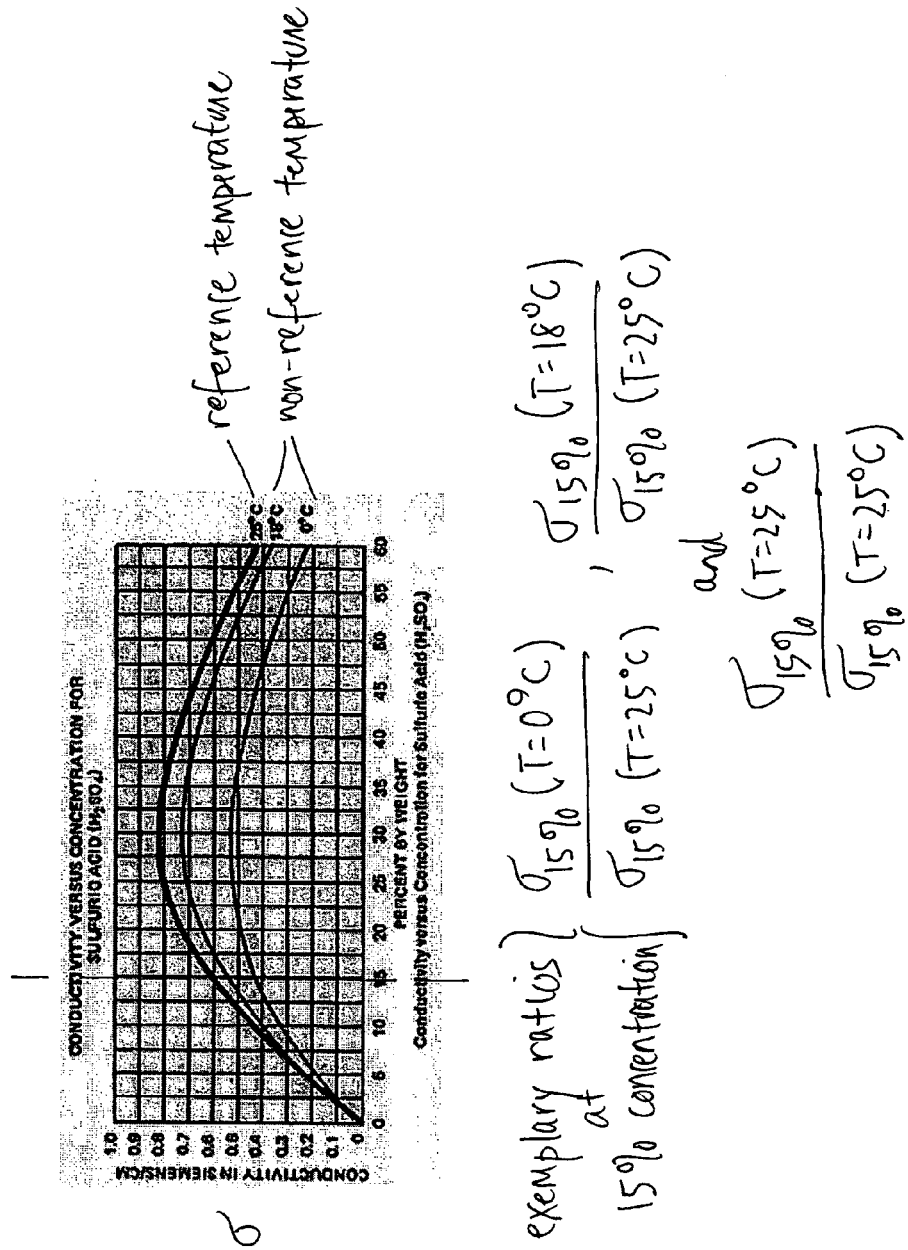
FIGS. 3 and 4 are flow diagrams that illustrate some features of the flow elements in the flow chart of FIG. 2.

FIG. 3 schematically illustrates features of FIG. 2's ratio determination 220 for sulfuric acid at a reference temperature of 25° C. and non-reference temperatures of 0° C. and 18° C., based on the data shown in FIG. 6. As shown in FIG. 3, for each of 0° C., 18° C., and 25° C. and each concentration, a ratio is determined between the conductivity at 0°/18°/25° C. and the conductivity at 25° C.

With continuing reference to FIG. 2, a relationship is then determined among the temperatures x, the absolute conductivities y, and the ratios z in the empirical data, to deduce an expression for the ratios z as a function f of the temperatures x and the absolute conductivities y, where $$z=f(x,y)$$

(230 in FIG. 2). The deduced expression z is the conversion factor for converting the absolute conductivity y of a solution at a solution temperature x to a compensated conductivity of the solution at the reference temperature.

Figure 4:
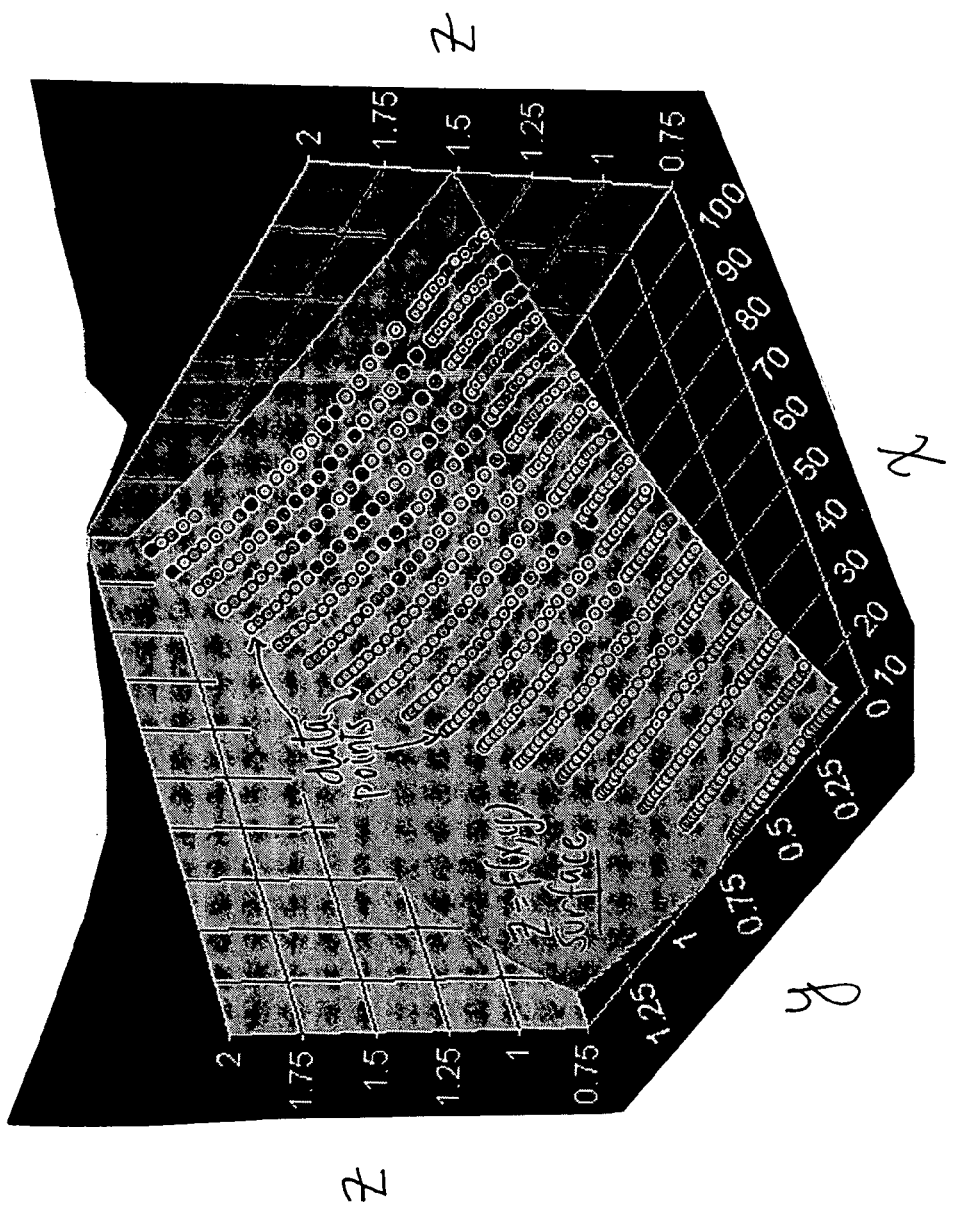

FIG. 4 schematically illustrates features of FIG. 2's expression determination 230 for sulfuric acid with a reference temperature of 25° C., where the values of x (° C.), y (Siemens/cm), and z (dimensionless) are based on Darling's empirical data. The expression for the ratio z is determined based on curve-fitting schemes known to those of ordinary skill in the art. For example, in some embodiments, the expression is determined by providing the x, y, and z data to a software package (such as a commercially available software packages) that can fit a three-dimensional function f to the data. One or more criteria may be considered in determining whether an expression proposed by the software package is a "good" fit to the data. Such criteria can include the value of $\chi^2$ or another criterion that quantifies the fit; the smoothness of the expression (relatively smooth expressions are preferable to expressions with unrealistic discontinuities); whether the value of z at the reference temperature remains near 1 in the expression; whether the expression is reversible, so that y may be expressed in terms of x and z, to thereby facilitate calibration of measurements of y, as described further below; the speed of computation with the expression; and/or other criteria that will be apparent to those of ordinary skill in the art.

As shown in the example embodiment of FIG. 4, the surface described by the following ratio of simple, non-orthogonal polynomials:

$$z=f(x,y)=(a+bx+cy)/(1+dx+ey)$$

is a mathematically "good" fit to the data for sulfuric acid, where the coefficients a, b, c, d, and e are floating point constants a=0.72531379, b=0.01881595, c=−0.49131471, d=0.0076371079, and e=−0.48257362. The expression shown in FIG. 4 is intended to be illustrative and non-limiting; those of ordinary skill in the art will recognize that other expressions (e.g., using non-simple and/or orthogonal polynomials) may be determined to be mathematically "good" fits to the empirical data under one or more criteria. The aforementioned FIG. 4 expression represents the conversion factor for converting the absolute conductivity y of a solution of sulfuric acid at a solution temperature x to a compensated conductivity y/z at a reference temperature of 25° C. Since the conversion factor depends on the solution's temperature and absolute conductivity, as opposed to only the solution's temperature as in present scenarios, the conversion factor permits the conversion factor itself, compensated conductivities, concentrations, and other related solution parameters to be determined with increased accuracy.

As an illustrative and non-limiting example of the accuracy of the disclosed systems and methods, consider two cases for sulfuric acid: (i) a first case in which solution temperature is 95° C. and absolute conductivity is 0.25 S/cm; and, (ii) a second case in which solution temperature is still 95° C., but absolute conductivity is 1.25 S/cm. Using the expression deduced above for sulfuric acid at a reference temperature of 25° C., the conversion factor for the first case is computed to be 1.489, while the conversion factor for the second case is 1.692. The difference between these factors is about 13%. In contrast to the disclosed systems and methods, present scenarios that compute conversion factors based solely on temperature predict the same factor for both cases.

As will be understood by those of ordinary skill in the art, the expression for the conversion factor that is deduced in FIG. 2 (230) is applicable to a single reference temperature, i.e., that temperature in the empirical data that is designated as the reference temperature (210). The expression cannot, therefore, be used for computations that involve a different reference temperature.

In some embodiments, the expression, i.e., the function f, including its form and the values of its coefficients (230) is stored for subsequent retrieval to determine a conversion factor (e.g., 130 in FIG. 1, 240 in FIG. 2).

Alternatively and/or in combination, in some embodiments, values of the expression are computed for a variety of absolute conductivities and temperatures (250 in FIG. 2) and stored in one or more data structures (e.g., look-up tables) for subsequent retrieval (e.g., 130 in FIG. 1, 260 in FIG. 2).

The inverse of the expression deduced in FIG. 2 (230) may be used to calibrate the absolute conductivity y of the solution (i.e., measurements of absolute conductivity y, FIG. 1 (110) and/or FIG. 2 (210)). In some embodiments, the absolute conductivity can be calibrated based on the following scheme. The absolute conductivity y of a known concentration of a solution of a given species is measured at a solution temperature x, and the compensated conductivity s=y/z of the concentration at a reference temperature is determined from a reference conductivity curve for the solution. Applying the compensated conductivity s=y/z and the solution temperature x to the inverse of the expression results in a predicted absolute conductivity y of the solution. The inverse can thus be understood as a conversion factor for converting the reference conductivity at a reference temperature to an estimated absolute conductivity at the solution temperature. For example, the inverse of FIG. 4's expression for sulfuric acid is the quadratic equation:

$$ey^2+y(1+dx-cs)-s(a+bx)=0,$$

where a, b, c, d, and e are constant coefficients, y is the predicted absolute conductivity, x is the solution temperature, and s is the compensated conductivity. The non-negative y solution to this equation is the predicted conductivity for the solution. The measurements of absolute conductivity can then be calibrated based on a measure of the difference (e.g., a difference, a root-mean-square difference, etc.) between the measured absolute conductivity and the predicted absolute conductivity.

Figure 5:
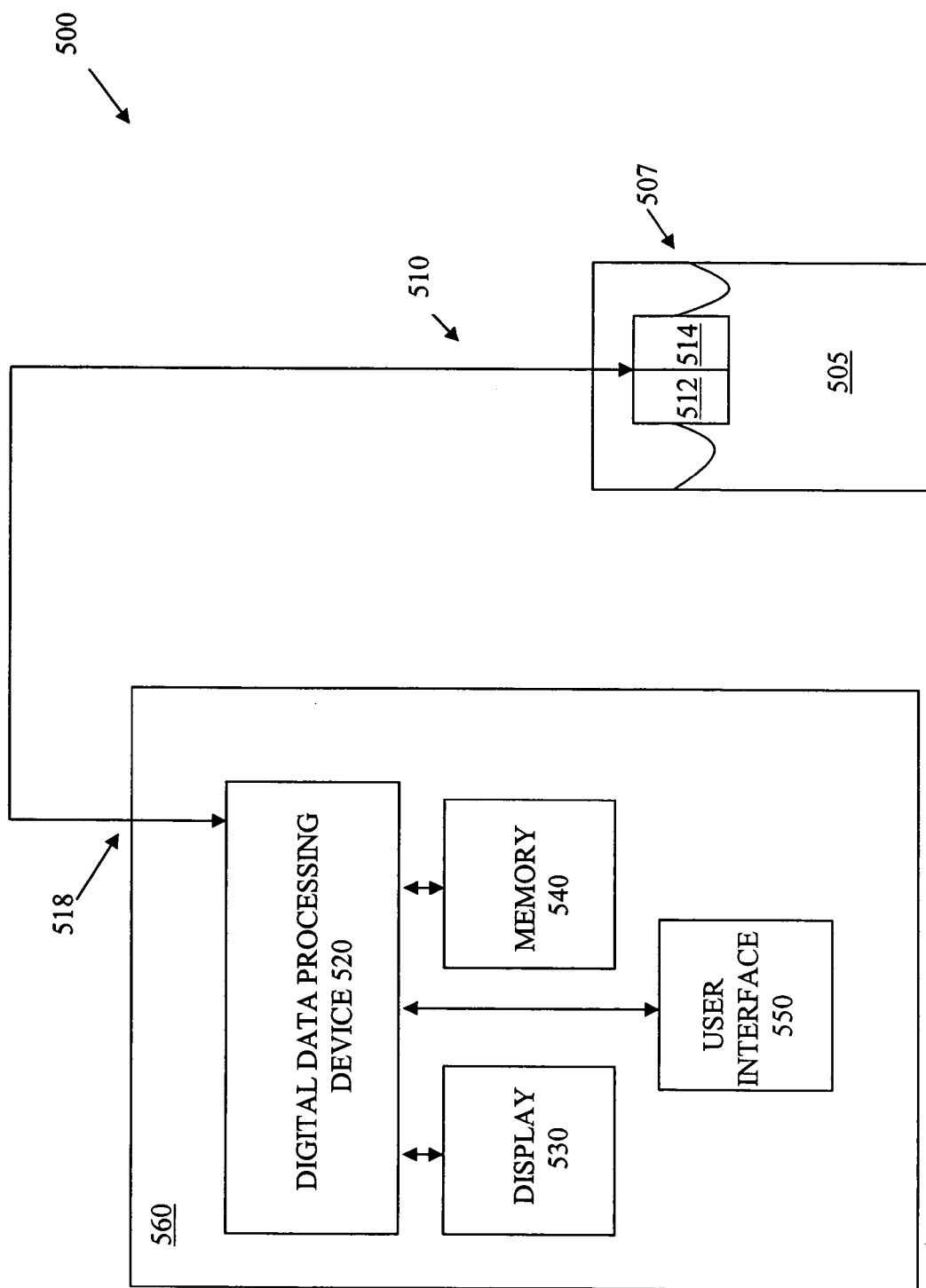
FIG. 5 schematically illustrates an exemplary system for determining a concentration of a solution; and, FIG. 6 shows reference conductivity curves for sulfuric acid.

FIG. 5 schematically illustrates an exemplary system 500 for determining a chemical concentration of a solution 505 that is disposed in a container 507. As shown in FIG. 5, the system 500 includes a probe 510 having sensors 512 and 514 for sensing the solution's temperature and conductivity, a digital data processing device 520 that is in communication with the probe 510, a display 530 in communication with the digital data processing device 520, a medium 540 (e.g., a memory) that can be accessed and/or read by the digital data processing device 520 and that includes reference data and instructions that cause the digital data processing device 520 to execute one or more of the previously described methods, and a user interface 550 in communication with the digital data processing device 520.

The sensors 512 and 514 may include sensors for detecting temperature and conductivity that are known to those of ordinary skill in the art. While the sensors 512 and 515 are shown as being disposed on single probe 510 in the embodiment of FIG. 5, the sensors 512 and 514 may be disposed on different probes in other embodiments.

The digital data processing device 520 is a processor-controlled device that is capable of receiving, processing, and/or transmitting digital data. It may include a personal computer (PC), a computer workstation (e.g., those manufactured by Sun or Hewlett-Packard), a laptop computer, a notebook computer, a server computer, a mainframe computer, a handheld device (e.g., a Pocket PC®), an information appliance, and/or another type of generic or special-purpose, processor-controlled device. A processor refers to the logic circuitry that responds to processes instructions that drive digital data processing devices and includes a central processing unit, an arithmetic logic unit, an application specific integrated circuit, a task engine, and/or combinations, arrangements, or multiples thereof.

The display 530 is a processor-controlled device that can visibly project at least numbers onto a display screen based on one or more projection schemes known to those of ordinary skill in the art. For example, the display may include a cathode ray tube, a liquid crystal display, a display based on light-emitting diodes, and a display based on a gas plasma.

The medium 540 is a processor-readable medium known to those of ordinary skill in the art, e.g., compact disk (CD), digital video disk (DVD), magnetic tape or disk, internal hard drive, external hard drive, random access memory (RAM), read-only memory (ROM), redundant array of independent disks (RAID), removable memory device, and/or any combination of the foregoing.

The user 550 interface includes a processor-controlled input device for interacting with a user. For example, the user interface may include a mouse, a keyboard, a touch sensitive screen, a track ball, a keypad, a stylus, and other input devices known to those of ordinary skill in the art.

In the shown embodiment, the digital data processing device 520, the display 530, the medium 540, and the user interface 550 are housed in an integrated unit 560 that includes a probe interface 518. Alternatively, one or more of these components may be housed separately from the other components and/or may be located remotely (e.g., across a network, such as LAN) from the other components.

In some embodiments, the system 500 may be packaged as an industrial process variable transmitter such as the INVENSYS®/FOXBORO® Model 875EC Intelligent Electrochemical Analyzer for Electrodeless Conductivity Measurements, and/or may include features that are similar to the INVENSYS®/FOXBORO® Model 875EC Intelligent Electrochemical Analyzer for Electrodeless Conductivity Measurements. The system 500 can include a two wire or a four wire configuration, or other configurations.

In most embodiments, medium 540 includes reference data and conversion factors for several different species of solution and several different reference temperatures, so that system 500 can be used by a user to determine concentrations and other related parameters for a variety of species of solution. The reference data includes the reference data described with respect to flow FIG. 1 (120), and the conversion factors include the expressions and/or the data structures (e.g., look-up tables) described with respect to flow FIG. 1 (130) and FIG. 2 (240, 260).

As will be understood by those of ordinary skill in the art, the disclosed systems and methods may be implemented without a display, such as the display 530 shown in FIG. 5. For example, in some embodiments, the disclosed systems and methods may be implemented with an alarm that is in communication with the digital data processing device 520. In one such embodiment, the digital data processing device 520 may activate the alarm (e.g., cause the alarm to emit a visible light signal and/or an audible noise, etc.) based on one or more of the temperature, the absolute conductivity, the conversion factor, the compensated conductivity, and the concentration (e.g., based on a value of one or more of the foregoing with respect to a pre-determined threshold). Also for example, in some embodiments, the digital data processing device 520 may be configured so as to provide data representing one or more of the temperature, the absolute conductivity, the conversion factor, the compensated conductivity, and the concentration to another digital data processing device (e.g., a device that controls system 500) via analog and/or digital telecommunications, industrial, and/or other communication standards and protocols.

An exemplary operation of system 500 will now be described. As will be understood by those of ordinary skill in the art, the disclosed systems and methods are not limited to the exemplary operation and can be implemented in operations that include features that are different than and/or additional to those described herein.

A user desiring to compute one or more parameters of the solution 505 determines the solution's species based on schemes known to those of ordinary skill in the art and provides an indication of that species (for example, sulfuric acid) to digital data processing device 520 via user interface 550. (In some embodiments, the memory 540 may include instructions for causing the digital data processing device 520 to determine that species.) The user then disposes the probe 510 and the sensors 512, 514 in the solution 505. Subsequently, the user and/or instructions in memory 540 cause the digital data processing device 520 to communicate with the sensors 512, 514, so as to determine the temperature and the absolute conductivity of the solution 505. The digital data processing device 520 may provide the sensed temperature and/or absolute conductivity to the display 530 for display thereon and observation by the user. Subsequently, the digital data processing device 520 determines a conversion factor, a compensated conductivity, a concentration, and/or another related parameter for the species of solution 505 based on reference data for the species and instructions stored on memory 540. (In some embodiments, the digital data processing device 520 calibrates the absolute conductivity based on the previously described methods prior to computing the solution parameter.) The digital data processing device 520 may provide the computed parameter to the display 530 for display thereon and observation thereby the user.

In some embodiments, the user specifies the parameter to be computed via the user interface 550. Alternatively and/or in combination, in some embodiments, the digital data processing device 520 is pre-configured to compute specific types of parameters.

Accordingly, systems and methods have been disclosed for determining temperature compensation factors based on solution temperature and absolute conductivity. These temperature compensation factors facilitate increased accuracy determinations of compensated conductivities, concentrations, and other related solution parameters.

The temperature compensation factors have been described as an intermediate in conversions from absolute conductivity to compensated conductivity or in determinations of concentration. As will be understood by those of ordinary skill in the art, the temperature compensation factors may, in some embodiments, not ever be computed. Rather, the temperature and conductivity dependence of the temperature compensation factors may be embodied in the compensated conductivity, the concentration, and/or another related solution parameter. In some embodiments, therefore, the disclosed systems and methods may be implemented so that the absolute conductivity is directly converted to compensated conductivity and/or so that the concentration or other related solution parameter is directly determined from absolute conductivity, without computing a temperature compensation factor. For example, in some embodiments, the empirical data in FIG. 2 (210, 220) can be used to form a two-dimensional look-up table for converting the conductivity of the solution at the temperature to a compensated conductivity of the solution at the reference temperature or a concentration of the solution. The two-dimensional look-up table includes a first dimension for the solution's temperature and a second dimension for the solution's absolute conductivity.

The systems and methods described herein are not limited to a hardware or software configuration; they can find applicability in many computing or processing environments. The systems and methods can be implemented in hardware or software, or in a combination of hardware and software. The systems and methods can be implemented in one or more computer programs, in which a computer program can be understood to comprise one or more processor-executable instructions. The computer programs can execute on one or more programmable processors, and can be stored on one or more storage media readable by the processor, comprising volatile and non-volatile memory and/or storage elements.

The computer programs can be implemented in high level procedural or object oriented programming language to communicate with a computer system. The computer programs can also be implemented in assembly or machine language. The language can be compiled or interpreted. The computer programs can be stored on a storage medium or a device (e.g., compact disk (CD), digital video disk (DVD), magnetic tape or disk, internal hard drive, external hard drive, random access memory (RAM), redundant array of independent disks (RAID), or removable memory device) that is readable by a general or special purpose programmable computer for configuring and operating the computer when the storage medium or device is read by the computer to perform the methods described herein.

Unless otherwise provided, references herein to memory can include one or more processor-readable and -accessible memory elements and/or components that can be internal to a processor-controlled device, external to a processor-controlled device, and/or can be accessed via a wired or wireless network using one or more communications protocols, and, unless otherwise provided, can be arranged to include one or more external and/or one or more internal memory devices, where such memory can be contiguous and/or partitioned based on the application.

Unless otherwise provided, references herein to a/the processor and a/the microprocessor can be understood to include one or more processors that can communicate in stand-alone and/or distributed environment(s) and can be configured to communicate via wired and/or wireless communications with one or more other processors, where such one or more processor can be configured to operate on one or more processor-controlled devices that can include similar or different devices. Use of such processor and microprocessor terminology can be understood to include a central processing unit, an arithmetic logic unit, an application-specific integrated circuit, and/or a task engine, with such examples provided for illustration and not limitation.

Unless otherwise provided, use of the articles "a" or "an" herein to modify a noun can be understood to include one or more than one of the modified noun.

While the systems and methods described herein have been shown and described with reference to the illustrated embodiments, those of ordinary skill in the art will recognize or be able to ascertain many equivalents to the embodiments described herein by using no more than routine experimentation. Such equivalents are encompassed by the scope of the present disclosure and the appended claims. Accordingly, the systems and methods described herein are not to be limited to the embodiments described herein, can include practices other than those described, and are to be interpreted as broadly as allowed under prevailing law.

What is claimed is:

1. A method for determining a concentration of a solution based on a conductivity of the solution at a temperature, the method comprising:
   providing reference conductivities of reference concentrations of the solution at a reference temperature,
   detecting the conductivity and the temperature of the solution,
   based on the detected conductivity and the detected temperature, determining a conversion factor for converting the detected conductivity of the solution at the detected temperature to a compensated conductivity of the solution at the reference temperature,
   based on the detected conductivity and the conversion factor, computing the compensated conductivity of the solution at the reference temperature,
   based on the compensated conductivity, the reference conductivities, and the reference concentrations, determining the concentration of the solution, and
   outputting the concentration of the solution.

2. The method of claim 1, wherein determining the conversion factor includes:
   providing pre-determined conversion factors that are associated with conductivities and temperatures of the solution,
   determining the conversion factor based on the pre-determined conversion factor that is associated with the detected conductivity and the detected temperature of the solution.

3. The method of claim 2, wherein providing pre-determined conversion factors include:
   providing the pre-determined conversion factors in at least one look-up table.

4. The method of claim 1, wherein determining the conversion factor includes:
   providing pre-determined conversion factors that are associated with conductivities and temperatures of the solution,
   determining whether one of the pre-determined conversion factors is associated with the detected conductivity and the detected temperature of the solution,
   based on one of the pre-determined conversion factors being associated with the detected conductivity and the detected temperature of the solution, determining the conversion factor to be the one of the pre-determined conversion factors, and
   based on none of the pre-determined values being associated with the detected conductivity and the detected temperature of the solution, determining the conversion factor based on interpolating between pre-determined conversion factors.

5. The method of claim 1, wherein determining the conversion factor includes:
   providing an expression for the conversion factor based on temperature and conductivity of the solution, and
   computing a value of the expression for the detected conductivity and the detected temperature of the solution.

6. The method of claim 5, wherein providing an expression for the conversion factor based on temperature and conductivity of the solution includes:
   generating the expression for the solution.

7. The method of claim 6, wherein generating the expression includes:
   at the reference temperature and non-reference temperatures, determining the conductivities of a group of different concentrations of the solution,
   for each non-reference temperature and each different concentration in the group, determining the ratio of the conductivity of the concentration at the non-reference temperature and the conductivity of the concentration at the reference temperature, and
   determining a relationship among the ratios, the conductivities of the different concentrations, and the temperatures.

8. The method of claim 6, wherein generating the expression includes:
   at the reference temperature and non-reference temperatures, determining the conductivities of a group of different concentrations of the solution,
   for each non-reference temperature and each different concentration in the group, determining the ratio of the conductivity of the concentration at the reference temperature and the conductivity of the concentration at the non-reference temperature, and
   determining a relationship among the ratios, the conductivities, and the temperatures.

9. The method of claim 1, wherein computing the compensated conductivity of the solution at the reference temperature includes:
   generating the compensated conductivity based on the product of the detected conductivity and the conversion factor.

10. The method of claim 1, wherein computing the compensated conductivity of the solution at the reference temperature includes:
    generating the compensated conductivity based on the product of the detected conductivity and the reciprocal of the conversion factor.

11. The method of claim 1, further comprising:
    prior to determining the conversion factor, calibrating the detected conductivity.

12. The method of claim 11, wherein calibrating includes:
    based on a reference conductivity of the solution at a reference temperature, determining a second conversion factor for converting the reference conductivity at the reference temperature to an estimated conductivity at the detected temperature,
    based on the reference conductivity and the second conversion factor, generating an estimated conductivity of the solution at the detected temperature, and
    calibrating the conductivity based on a measure of the difference between the detected conductivity and the estimated conductivity.

13. A device for determining a concentration of a solution based on a conductivity of the solution at a temperature, the device comprising:
    at least one digital data processing device receiving inputs of the conductivity and temperature of the solution and in communication with reference conductivities of reference concentrations of the solution at a reference temperature and configured for:
    based on the conductivity and the temperature, determining a conversion factor for converting the conductivity of the solution at the temperature to a compensated conductivity of the solution at the reference temperature, based on the conductivity and the conversion factor, computing the compensated conductivity of the solution at the reference temperature, based on the compensated conductivity, the reference conductivities, and the reference concentrations, determining the concentration of the solution and outputting the concentration of the solution.

14. The device of claim 13, wherein the at least one digital data processing device is in communication with pre-determined conversion factors that are associated with conductivities and temperatures of the solution and is configured for determining the conversion factor based on:

determining whether one of the pre-determined conversion factors is associated with the conductivity and the temperature of the solution, based on one of the pre-determined conversion factors being associated with the conductivity and the temperature of the solution, determining the conversion factor to be the one of the pre-determined conversion factors, and based on none of the pre-determined values being associated with the conductivity and the temperature of the solution, determining the conversion factor based on interpolating between pre-determined conversion factors.

15. The device of claim 13, wherein the at least one digital data processing device is in communication with an expression for the conversion factor based on temperature and conductivity of the solution and is configured for determining the conversion factor based on:

computing a value of the expression for the conductivity and the temperature of the solution.

16. A processor-readable medium including instructions for determining a concentration of a solution based on a conductivity of the solution at a temperature and reference conductivities of reference concentrations of the solution at a reference temperature, the processor-readable medium including instructions to cause a processor to:

receive inputs of the conductivity and temperature of the solution, based on the conductivity and the temperature, determine a conversion factor for converting the conductivity of the solution at the temperature to a compensated conductivity of the solution at the reference temperature, based on the conductivity and the conversion factor, compute the compensated conductivity of the solution at the reference temperature, based on the compensated conductivity, the at least one reference conductivity, and the at least one reference concentration, determine the concentration of the solution, and output the concentration of the solution.

17. The processor-readable medium of claim 16, further including:

pre-determined conversion factors that are associated with conductivities and temperatures of the solution, and instructions to cause the processor to:

determine whether one of the pre-determined conversion factors is associated with the conductivity and the temperature of the solution, based on one of the pre-determined conversion factors being associated with the conductivity and the temperature of the solution, determine the conversion factor to be the one of the pre-determined conversion factors, and based on none of the pre-determined values being associated with the conductivity and the temperature of the solution, determine the conversion factor based on interpolating between pre-determined conversion factors.

18. The processor-readable medium of claim 16, further including:

an expression for the conversion factor based on temperature and conductivity of the solution, and instructions to cause the processor to compute a value of the expression for the conductivity and the temperature of the solution.

19. A system for determining a concentration of a solution, the system comprising:

at least one temperature sensor for detecting a temperature of the solution, at least on conductivity sensor for detecting a conductivity of the solution, at least one digital data processing device in communication with the at least one temperature sensor and the at least one conductivity sensor, and at least one medium that is capable of being read by the at least one digital data processing device and that includes:

reference conductivities of reference concentrations of the solution, and instructions for causing the at least one digital data processing device to:

based on the conductivity and the temperature, determine a conversion factor for converting the conductivity of the solution at the temperature to a compensated conductivity of the solution at a reference temperature, based on the conductivity and the conversion factor, compute the compensated conductivity of the solution at the reference temperature, based on the compensated conductivity, the at least one reference conductivity, and the at least one reference concentration, determine the concentration of the solution.

20. The system of claim 19, wherein the at least one medium further includes:

pre-determined conversion factors that are associated with conductivities and temperatures of the solution, and instructions for causing the digital data processing device to:

determine whether one of the pre-determined conversion factors is associated with the conductivity and the temperature of the solution, based on one of the pre-determined conversion factors being associated with the conductivity and the temperature of the solution, determine the conversion factor to be the one of the pre-determined conversion factors, and based on none of the pre-determined values being associated with the conductivity and the temperature of the solution, determine the conversion factor based on interpolating between pre-determined conversion factors.

21. The system of claim 19, wherein the at least one medium further includes:

an expression for the conversion factor based on temperature and conductivity of the solution, and instructions for causing the digital data processing device to compute a value of the expression for the conductivity and the temperature of the solution.

22. The system of claim 19, further comprising:
at least one display in communication with the at least one digital data processing device,
wherein the at least one medium further includes instructions for causing the at least one digital data processing device to provide data representing at least one of the detected temperature, the detected conductivity, the compensated conductivity, and the concentration to the display for display thereon.

23. The system of claim 19, further comprising:
at least one alarm in communication with the at least one digital data processing device,
wherein the at least one medium further includes instructions for causing the at least one digital data processing device to activate the at least one alarm based on at least one of the detected temperature, the detected conductivity, the compensated conductivity, and the concentration.

24. The system of claim 19, wherein the at least one medium further includes instructions for causing the at least one digital data processing device to provide data representing at least one of the detected temperature, the detected conductivity, the compensated conductivity, and the concentration to a different digital data processing device.

25. A method for determining a compensated conductivity of a solution at a reference temperature, the method comprising:
detecting a conductivity and a temperature of the solution,
based on the conductivity and the temperature, determining a conversion factor for converting the conductivity of the solution at the temperature to a compensated conductivity of the solution at the reference temperature,
based on the conductivity and the conversion factor, computing the compensated conductivity of the solution at the reference temperature, and
outputting the compensated conductivity of the solution.

26. A method for determining a compensated conductivity of a solution at a reference temperature, the method comprising:
detecting a conductivity and a temperature of the solution,
providing at least one two-dimensional look-up table for converting the conductivity of the solution at the temperature to a compensated conductivity of the solution at the reference temperature, in which the two-dimensional look-up table includes a first dimension for temperature and a second dimension for conductivity,
based on the two-dimensional look-up table, computing the compensated conductivity of the solution at the reference temperature, and
outputting the compensated conductivity of the solution.

27. A method for determining a concentration of a solution, the method comprising:
providing at least one two-dimensional look-up table of conversion factors for converting a conductivity of the solution at a temperature to a concentration of the solution, in which the two-dimensional look-up table includes a first dimension for temperature and a second dimension for conductivity,
detecting the conductivity and the temperature of the solution,
based on the conductivity and the temperature of the solution, determining a compensated conductivity at a reference temperature,
based on a conversion factor determined from the at least one two-dimensional look-up table for the compensated conductivity and the temperature, computing the concentration of the solution, and
outputting the concentration of the solution.

* * * * *